United States Patent [19]

Lee

[11] 4,427,699
[45] Jan. 24, 1984

[54] IMIDOYL THIOUREAS AS USED TO CONTROL TOBACCO BUDWORM

[75] Inventor: David L. Lee, Martinez, Calif.

[73] Assignee: Stauffer Chemical Company, Westport, Conn.

[21] Appl. No.: 410,188

[22] Filed: Aug. 23, 1982

[51] Int. Cl.$^3$ .................. A61K 31/17; C07C 157/09
[52] U.S. Cl. ........................................ 424/322; 564/27
[58] Field of Search .......................... 564/27; 424/322

[56] References Cited

U.S. PATENT DOCUMENTS

| | | | |
|---|---|---|---|
| 2,161,754 | 6/1939 | Watt | 564/27 X |
| 3,898,277 | 8/1975 | Duerr et al. | 564/27 |
| 3,984,467 | 10/1976 | Diana | 564/27 X |
| 4,011,343 | 3/1977 | Leeming et al. | 564/27 X |
| 4,150,160 | 4/1979 | Drabek et al. | 424/322 |

OTHER PUBLICATIONS

Goerdeler et al., Chem. Ber. 1979, 112 (4), 1288-1296.

Primary Examiner—Thomas A. Waltz
Attorney, Agent, or Firm—Edwin H. Baker

[57] ABSTRACT

Compounds of the formula

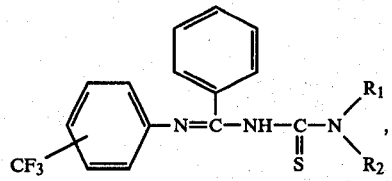

wherein $R_1$ is hydrogen or $C_1$-$C_4$ alkyl, and $R_2$ is $C_1$-$C_4$ alkyl, which are useful for controlling tobacco budworm.

9 Claims, No Drawings

IMIDOYL THIOUREAS AS USED TO CONTROL TOBACCO BUDWORM

DESCRIPTION OF THE INVENTION

This invention relates to certain novel imidoyl thioureas and their use in controlling tobacco budworm [Heliothis virescens (Fabricius)].

The compounds of the present invention have the structural formula

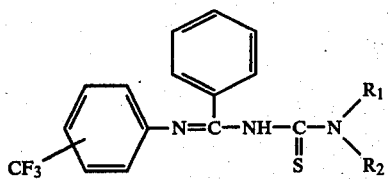

wherein $R_1$ is hydrogen or $C_1$–$C_4$ alkyl, preferably hydrogen; $R_2$ is $C_1$–$C_4$ alkyl and the trifluoromethyl group preferably is in the meta position.

The term "alkyl" includes both straight and branched-chain configurations; for example, methyl, ethyl, n-propyl, isopropyl, n-butyl, isobutyl, and tert-butyl.

BACKGROUND OF THE INVENTION

U.S. Pat. No. 3,629,455 describes a method of controlling hookworms and tapeworms with 1-phenyl-3-alkanimidoylureas having the formula

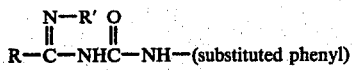

where R is alkyl; and R′ is hydrogen or lower alkyl.

U.S. Pat. No. 4,039,575 describes 1-phenyl-3-alkanimidoylthioureas having the formula

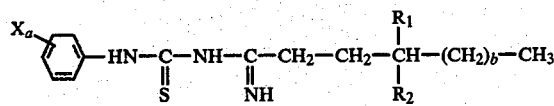

wherein X is 2-, 3-, or 4-chloro, 2- or 4-bromo, 4-fluoro, 4-iodo, 4-methyl, 4-methoxy, or 4-trifluoromethoxy; a is 1 or 2; $R_1$ and $R_2$ are both hydrogen or methyl; and b is 0–4; acid-addition salts thereof; and compositions thereof.

U.S. Pat. No. 3,699,110 describes pyridylaminidinoureas having the formula

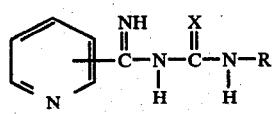

wherein x is oxygen or sulfur and R is alkyl having from 1 through 8 carbon atoms, alkenyl having from 3 through 6 carbon atoms, cycloalkyl having 3 through 6 carbon atoms, phenyl or benzyl. The terms "benzyl" and "phenyl" include substituted and unsubstituted aryl groups. Representative ring substituents are halo, nitro, trichloromethyl, methyl and the like. The alkyl group in these compounds can be methyl, ethyl, normal propyl, isopropyl, normal butyl, secondary butyl, tertiary butyl, normal pentyl, isopentyl and the various forms of hexyl, heptyl and octyl.

DESCRIPTION OF THE INVENTION

The compounds of the present invention are prepared by the following general method.

Reaction No. 1

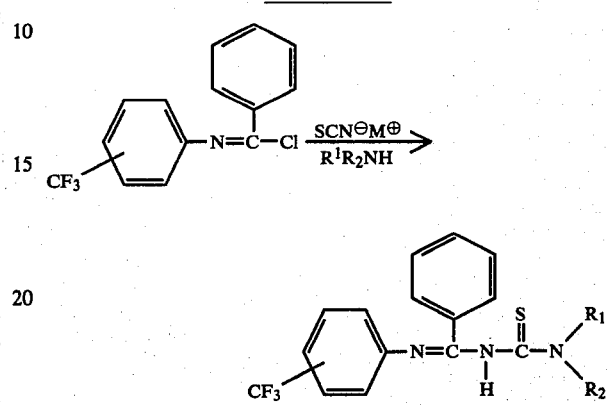

wherein $R_1$ is hydrogen or $C_1$–$C_4$ alkyl; $R_2$ is $C_1$–$C_4$ alkyl and M is sodium or potassium.

In the above reaction, excess sodium or potassium thiocyanate is dissolved in a solvent; for example acetone, dimethyl sulfoxide, or tetrahydrofuran. The solution is cooled to between 0°–5° C. before adding a mole amount of the appropriate imidoyl chloride at a rate such that the temperature does not exceed 5° C. The imidoyl chloride may be prepared by reacting thionyl chloride with the appropriate amide as described in J. Goerdeler andd H. Lohmann, Chemische Berichte, 110, pp. 2996–3009 (1977)). After stirring an additional hour at 0°–5° C., the appropriate amine is added in excess and at a rate such that the temperature does not exceed 5° C. The solution is again stirred one hour at 0°–5° C., then water (200 ml/mole of imidoyl chloride) is added to dissolve any inorganic salts. The resultant precipitate is isolated by filtration and recrystallization from ethanol to give the reaction product.

Preparation of the compounds of this invention is illustrated by the following example.

EXAMPLE 1

N-Propyl-N′-(N-m-trifluoromethylphenyl-benzimidoyl)thiourea

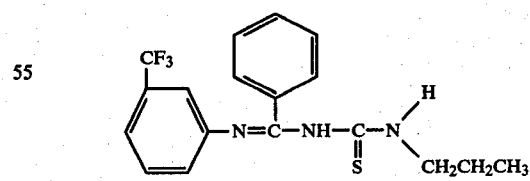

Sodium thiocyanate 22.3 grams (g) (0.275 mole) was dissolved in 250 ml of acetone in a 500 ml, 3-necked, round-bottom flask equipped with a mechanical stirrer. The mixture was stirred well and cooled to 0°–5° C. before adding 71 g of N-(m-trifluoromethylphenyl)benzimidoyl chloride (0.25 mole) dropwise over a period of one hour. The solution was stirred an additional hour at 0°–5° C., then 29.5 g of n-propylamine (0.5 mole) was added over a period of 45 minutes. The mixture was again stirred for one hour at 0°–5° C. Next, 50 ml of water was added, and the resultant precipitate was isolated by filtration and recrystallization from ethanol to produce 32.5 g of white solid in a needle-like form, m.p. 134°–136° C. The overall yield was 35.6%.

The structure was confirmed by proton nuclear magnetic resonance, infrared, and mass spectroscopy.

The following is a table of compounds active in controlling tabacco budworm and preparable according to the procedures described above.

TABLE 1

| Compound Number | $R_1$ | $R_2$ | Physical Constant $n_D^{30}$ m.p. °C. |
|---|---|---|---|
| 1[a] | H | n-$C_3H_7$ | 134–136 |
| 2 | H | i-$C_3H_7$ | 155–163 |
| 3 | H | t-$C_4H_9$ | 139–141 |
| 4 | H | —$C_2H_5$ | 144–147 |
| 5 | —$CH_3$ | —$CH_3$ | 151–153.5 |

[a] = Prepared in Example I.

The compounds listed in Table 1 were evaluated for their ability to control tobacco budworm by using the following test.

Test compounds were diluted in a 50—50 acetone-water solution. Sections of Romaine lettuce (*Latuca sativa*) leaves, approximately 1×1.5 inches (2.54×3.81 cm) were immersed in the test solutions for 2–3 seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe any delayed effects of the test chemicals.

Test compounds were first screened at a concentration of 0.1% of the solution. Compounds exhibiting activity were further tested at decreasing concentrations to obtain an LD-50 value (the concentration at which approximately 50% mortality occurs) for the compound. The LD-50 values are shown in Table II below under the heading "% Test Compound of Total Solution."

TABLE II

| Number | % Test Compound of Total Solution |
|---|---|
| 1 | 0.01 |
| 2 | 0.03 |
| 3 | 0.03 |
| 4 | 0.03 |
| 5 | 0.05 |

In general, inert adjuvants are combined with the active compound to make emulsions, suspensions, solutions, dusts, aerosol sprays, or other forms of the compound which are suitable for conventional application. These compositions may include a single active compound of this invention as the tobacco budworm-controlling component or an admixture of other compounds having similar utility. The tobacco budworm-controlling compositions of this invention can contain (a) liquid adjuvants, such as organic solvents, sesame oil, xylene range solvents, heavy petroleum, etc.; (2) emulsifying agents; (c) surface active agents; (d) solid adjuvants such as talc; phyrophyllite, diatomite; gypsum; clays; or (e) propellants, such as dichlorodifluoromethane, etc. If desired, the active compounds can also be applied directly to feedstuffs, seeds, etc., or to other materials upon which the tobacco budworm feeds.

The presently disclosed compounds need not be inherently active; the purposes of this invention will be fully served if the compound is rendered active by external influences, such as light, or by physiological action occurring after the tobacco budworm ingests the compound.

The precise manner in which the compositions of this invention are used in any particular instance will be readily apparent to a person skilled in the art. Generally, the active compound will be formulated in a liquid composition; for example, an emulsion, suspension, or aerosol spray. While the concentration of the active compound in the aforesaid compositions can vary within wide limits, ordinarily the active compound will comprise between about 1.0 and about 95% by weight of the compositions and preferably between about 5% to 80% by weight.

What is claimed is:

1. Compounds having the structural formula

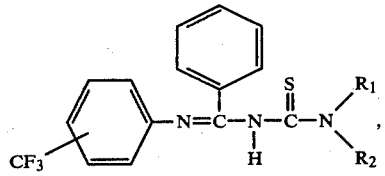

wherein $R_1$ is hydrogen or $C_1$–$C_4$ alkyl, and $R_2$ is $C_1$–$C_4$ alkyl.

2. The compound of claim 1 wherein the trifluoromethyl group is in the meta-position.

3. The compound according to claim 2 wherein $R_1$ is hydrogen and $R_2$ is n-propyl.

4. The compound according to claim 2 wherein $R_1$ is hydrogen and $R_2$ is isopropyl.

5. The compound according to claim 2 wherein $R_1$ is hydrogen and $R_2$ is tert-butyl.

6. The compound according to claim 2 wherein $R_1$ is hydrogen and $R_2$ is ethyl.

7. The compound according to claim 2 wherein $R_1$ is methyl and $R_2$ is methyl.

8. The method of controlling tobacco budworm comprising applying to the habitat thereof an effective amount of a compound of the formula

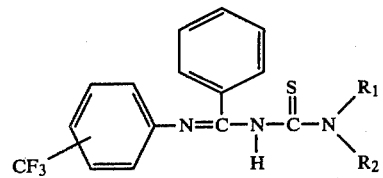

wherein $R_1$ is hydrogen or $C_1$–$C_4$ alkyl, and $R_2$ is $C_1$–$C_4$ alkyl.
9. The composition useful for controlling tobacco budworm comprising an effective amount of a compound of the formula
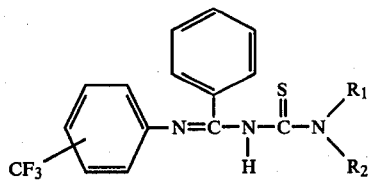
wherein $R_1$ is hydrogen or $C_1$–$C_4$ alkyl, and $R_2$ is $C_1$–$C_4$ alkyl, and an inert carrier therefor.
* * * * *